(12) United States Patent
Altavilla et al.

(10) Patent No.: US 10,391,114 B2
(45) Date of Patent: *Aug. 27, 2019

(54) THERAPEUTIC COMBINATIONS OF CURCUMINOIDS AND FLAVONOIDS

(71) Applicant: Primus Pharmaceuticals, Inc., Scottsdale, AZ (US)

(72) Inventors: Domenica Altavilla, Messina (IT); Robert Levy, Cave Creek, AZ (US)

(73) Assignee: Primus Pharmaceuticals, Inc., Scottsdale, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/353,902

(22) Filed: Nov. 17, 2016

(65) Prior Publication Data
US 2017/0136052 A1 May 18, 2017

Related U.S. Application Data

(60) Provisional application No. 62/256,228, filed on Nov. 17, 2015.

(51) Int. Cl.
| | | |
|---|---|---|
| *A61K 31/7048* | (2006.01) | |
| *A61K 31/353* | (2006.01) | |
| *A61K 31/12* | (2006.01) | |
| *A61K 9/00* | (2006.01) | |
| *A61K 45/06* | (2006.01) | |

(52) U.S. Cl.
CPC ........ *A61K 31/7048* (2013.01); *A61K 9/0053* (2013.01); *A61K 31/12* (2013.01); *A61K 31/353* (2013.01); *A61K 45/06* (2013.01)

(58) Field of Classification Search
CPC .. A61K 31/7048; A61K 31/353; A61K 31/12; A61K 9/0053
See application file for complete search history.

(56) References Cited

U.S. PATENT DOCUMENTS

| | | | | |
|---|---|---|---|---|
| 2009/0304827 A1* | 12/2009 | Kim | ........................ | A61K 31/12 424/725 |
| 2010/0179103 A1* | 7/2010 | Desai | ............... | A61K 47/48969 514/58 |
| 2010/0190733 A1* | 7/2010 | Squadrito | ............ | A61K 31/352 514/27 |
| 2013/0210753 A1 | 8/2013 | Squadrito et al. | | |

OTHER PUBLICATIONS

Aditya et al., Food Chemistry, 2015, 173, p. 7-13, Available online Sep. 30, 2014. (Year: 2015).*

Lorenz W, Buhrmann C, Mobasheri A, Lueders C, Shakibaei M. Bacterial lipopolysaccharides form procollagen-endotoxin complexes that trigger cartilage inflammation and degeneration: implications for the development of rheumatoid arthritis. Arthritis Res Ther. 2013;15(5):R111.

Bitto A, Squadrito F, Irrera N, Pizzino G, Pallio G, Mecchio A, Galfo F, Altavilla D. Flavocoxid, a nutraceutical approach to blunt inflammatory conditions. Mediators Inflamm. 2014;2014:790851.

Burnett, B.P.; Bitto, A.; Altavilla, D.; Squadrito, F.; Levy, R.M.; Pillai, L. Flavocoxid inhibits phospholipase A2, peroxidase moieties of the cyclooxygenase (COX) and 5-lipoxygenase, modifies COX-2 gene expression and acts as an antioxidant. Mediators of Inflammation, 2011:385780. doi: 10.1155/2011/385780.

Levy, R.; Khokhlov, A.; Kopenkin, S.; Bart, B.; Ermolova, T.; Kantemirova, R.; Mazurov, V.; Bell, M.; Caldron, R; Pillai, L.; Burnett, B. Efficacy and safety of flavocoxid compared with naproxen in subjects with osteoarthritis of the knee—a subset analysis Adv. Ther., 2010, 27(12), 953-962.

Henrotin Y Henrotin Y, Clutterbuck AL, Allaway D, Lodwig EM, Hanis P, Mathy-Hartert M, Shakibaei M, Mobasheri A. Biological actions of curcumin on articular chondrocytes. Osteoarthritis Cartilage. Feb. 2010;18(2):141-149.

Altavilla D, Squadrito F, Bitto A, Polito F, Burnett BP, Di Stefano V,Minutoli L. Flavocoxid, a dual inhibitor of cyclooxygenase and 5-lipoxygenase,blunts proinflammatory phenotype activation in endotoxin-stimulated macrophages. Br J Pharmacol. Aug. 2009;157(8):1410-8.

Livak, K. J. and T. D. Schmittgen, 2001. Analysis of relative gene expression data using real-time quantitative PCR and the 2(-Delta Delta C(T)) Method. Methods 25:402-408.

Tsuchida Al, Beekhuizen M, 't Hart MC, Radstake TR, Dhert WJ, Saris DB, van Osch GJ, Creemers LN. Cytokine profiles in the joint depend on pathology, but are different between synovial fluid, cartilage tissue and cultured chondrocytes. Arthritis Res Ther. Sep. 26, 2014;16(5):441.

* cited by examiner

*Primary Examiner* — Jonathan S Lau
(74) *Attorney, Agent, or Firm* — Clark Sullivan

(57) ABSTRACT

Provided is a formulation and a method associated therewith for treating inflammation. The formulation includes therapeutically effective amounts of curcuminoids and two flavonoids. The two flavonoids include baicalin and catechin.

8 Claims, 21 Drawing Sheets

NF-kB(p50)

| CTR | LPS 2μg/ml | LPS+ FL16μg/ml | LPS+ FL32μg/ml | LPS+ CUR5 μg/ml | LPS+CUR5+ FL16 μg/ml | LPS+CUR5+ FL32μg/ml | LPS+ CUR10μg/ml | LPS+CUR10+ FL16μg/ml | LPS+CUR10+ FL32μg/ml |
|---|---|---|---|---|---|---|---|---|---|
| 0.05 | 0.48 | 0.53 | 0.57 | 0.47 | 0.36 | 0.23 | 0.25 | 0.26 | 0.25 |
| 0.06 | 0.49 | 0.56 | 0.56 | 0.42 | 0.43 | 0.32 | 0.27 | 0.27 | 0.26 |
| -0.02 | 0.43 | 0.49 | 0.51 | 0.41 | 0.38 | 0.21 | 0.19 | 0.18 | 0.17 |
| -0.11 | 0.32 | 0.38 | 0.46 | 0.35 | 0.39 | 0.12 | 0.1 | 0.07 | 0.07 |
| -0.08 | 0.25 | 0.31 | 0.35 | 0.22 | 0.32 | 0.16 | 0.12 | 0.1 | 0.13 |
| 0.1 | 0.53 | 0.58 | 0.63 | 0.52 | 0.53 | 0.32 | 0.3 | 0.29 | 0.31 |

FIG. 10

| NF-kB(p65) | | | | | | | | | |
|---|---|---|---|---|---|---|---|---|---|
| CTR | LPS 2μg/ml | LPS+ FL16μg/ml | LPS+ FL32μg/ml | LPS+ CUR5 μg/ml | LPS+CUR5+ FL16 μg/ml | LPS+CUR5+ FL32μg/ml | LPS+ CUR10μg/ml | LPS+CUR10+ FL16μg/ml | LPS+CUR10+ FL32μg/ml |
| 0.04 | 0.2 | 0.17 | 0.14 | 0.18 | 0.16 | 0.2 | 0.06 | 0.08 | 0.02 |
| 0.04 | 0.24 | 0.19 | 0.18 | 0.19 | 0.18 | 0.18 | 0.1 | 0.05 | 0.02 |
| -0.03 | 0.14 | 0.13 | 0.11 | 0.11 | 0.12 | 0.12 | -0.02 | 0.04 | -0.02 |
| -0.05 | 0.12 | 0.07 | 0.06 | 0.06 | 0.05 | 0.08 | 0.1 | -0.01 | -0.03 |
| -0.02 | 0.13 | 0.1 | 0.08 | 0.09 | 0.07 | 0.08 | 0.125 | -0.02 | -0.04 |
| 0.02 | 0.22 | 0.17 | 0.15 | 0.17 | 0.16 | 0.17 | 0.07 | 0.08 | 0.03 |

| | CTR | LPS 2μg/ml | LPS+ FL16μg/ml | LPS+ FL32μg/ml | LPS+ CUR5 μg/ml | LPS+CUR5+ FL16 μg/ml | LPS+CUR5+ FL32μg/ml | LPS+ CUR10μg/ml | LPS+CUR10+ FL16μg/ml | LPS+CUR10+ FL32μg/ml |
|---|---|---|---|---|---|---|---|---|---|---|
| | 0.04 | 3.31 | 3.2 | 3.27 | 2.4 | 2.15 | 1.14 | 0.82 | 0.87 | 0.86 |
| | 0.11 | 3.5 | 3.4 | 3.42 | 2.45 | 2.21 | 1.01 | 0.94 | 0.92 | 0.81 |
| | -0.15 | 2.9 | 2.71 | 2.75 | 2.1 | 1.91 | 1.03 | 0.63 | 0.6 | 0.63 |
| | -0.12 | 3.11 | 2.92 | 3.05 | 2.39 | 2 | 0.94 | 0.73 | 0.7 | 0.68 |
| | -0.11 | 3.13 | 3.22 | 3.08 | 2.32 | 2.12 | 1.03 | 0.71 | 0.81 | 0.78 |
| | 0.03 | 3.43 | 3.11 | 3.45 | 2.2 | 1.9 | 0.92 | 0.74 | 0.94 | 0.77 |

FIG. 12

MMP-1

| | LPS 2μg/ml | LPS+FL16μg/ml | LPS+FL32μg/ml | LPS+CUR5μg/ml | LPS+CUR5+FL16 μg/ml | LPS+CUR5+FL32μg/ml | LPS+CUR10μg/ml | LPS+CUR10+FL16μg/ml | LPS+CUR10+FL32μg/ml |
|---|---|---|---|---|---|---|---|---|---|
| CTR | | | | | | | | | |
| 0.07 | 1.19 | 1.2 | 1.21 | 0.9 | 0.78 | 0.38 | 0.33 | 0.22 | 0.22 |
| 0.05 | 1.27 | 1.26 | 1.27 | 0.92 | 0.86 | 0.42 | 0.38 | 0.3 | 0.28 |
| -0.1 | 0.9 | 0.95 | 0.93 | 0.65 | 0.56 | 0.21 | 0.21 | 0.17 | 0.12 |
| -0.03 | 0.77 | 0.78 | 0.77 | 0.5 | 0.47 | 0.18 | 0.15 | 0.06 | -0.01 |
| -0.05 | 0.84 | 0.85 | 0.91 | 0.61 | 0.59 | 0.25 | 0.22 | 0.15 | 0.06 |
| 0.06 | 1.2 | 1.31 | 1.3 | 0.95 | 0.87 | 0.46 | 0.41 | 0.25 | 0.27 |

FIG. 13

| MMP-3 | LPS 2µg/ml | LPS+ FL16µg/ml | LPS+ FL32µg/ml | LPS+ CUR5 µg/ml | LPS+CUR5+ FL16 µg/ml | LPS+CUR5+ FL32µg/ml | LPS+ CUR10µg/ml | LPS+CUR10+ FL16µg/ml | LPS+CUR10+ FL32µg/ml |
|---|---|---|---|---|---|---|---|---|---|
| CTR | | | | | | | | | |
| 0.07 | 1.52 | 1.36 | 1.41 | 1.14 | 1.06 | 0.92 | 0.23 | 0.1 | 0.08 |
| 0.08 | 1.66 | 1.47 | 1.52 | 1.3 | 1.15 | 1.02 | 0.3 | 0.18 | 0.14 |
| -0.12 | 1.25 | 1.15 | 1.12 | 0.85 | 0.74 | 0.56 | -0.02 | -0.05 | -0.1 |
| -0.05 | 1.12 | 0.95 | 0.99 | 0.76 | 0.63 | 0.34 | -0.01 | -0.08 | -0.12 |
| -0.08 | 1.06 | 0.87 | 0.87 | 0.68 | 0.47 | 0.42 | -0.05 | -0.15 | -0.14 |
| 0.1 | 1.56 | 1.29 | 1.46 | 1.19 | 1.01 | 0.94 | 0.33 | 0.21 | 0.16 |

FIG. 14

MMP-9

| | CTR | LPS 2ug/ml | LPS+ FL16ug/ml | LPS+ FL32ug/ml | LPS+ CUR5ug/ml | LPS+CUR5+ FL16 ug/ml | LPS+CUR5+ FL32ug/ml | LPS+ CUR10ug/ml | LPS+CUR10+ FL16ug/ml | LPS+CUR10+ FL32ug/ml |
|---|---|---|---|---|---|---|---|---|---|---|
| | 0.09 | 1.62 | 1.71 | 1.4 | 0.63 | 0.61 | 0.69 | 0.58 | 0.47 | 0.27 |
| | 0.07 | 1.6 | 1.75 | 1.29 | 0.5 | 0.56 | 0.59 | 0.58 | 0.25 | 0.14 |
| | -0.1 | 1.27 | 1.51 | 1.13 | 0.31 | 0.26 | 0.35 | 0.31 | 0.22 | -0.07 |
| | -0.05 | 1.25 | 1.31 | 1.23 | 0.33 | 0.38 | 0.45 | 0.34 | 0.16 | -0.01 |
| | -0.12 | 1.29 | 1.47 | 1.17 | 0.33 | 0.34 | 0.38 | 0.35 | 0.2 | -0.04 |
| | 0.11 | 1.53 | 1.59 | 1.33 | 0.63 | 0.63 | 0.82 | 0.73 | 0.32 | 0.18 |

FIG. 15

| MMP-13 | LPS 2μg/ml | LPS+ FL16μg/ml | LPS+ FL32μg/ml | LPS+ CUR5 μg/ml | LPS+CUR5+ FL16 μg/ml | LPS+CUR5+ FL32μg/ml | LPS+ CUR10μg/ml | LPS+CUR10+ FL16μg/ml | LPS+CUR10+ FL32μg/ml |
|---|---|---|---|---|---|---|---|---|---|
| CTR |  |  |  |  |  |  |  |  |  |
| 0.12 | 2.53 | 2.46 | 2.5 | 1.36 | 1.25 | 1.24 | 2.17 | 2.61 | 2.14 |
| 0.02 | 2.51 | 2.49 | 2.51 | 1.43 | 1.08 | 1.09 | 2.2 | 2.25 | 2.17 |
| -0.06 | 2.24 | 2.24 | 2.22 | 1.12 | 0.8 | 0.83 | 1.86 | 1.96 | 1.83 |
| -0.09 | 2.28 | 2.23 | 2.2 | 1.18 | 0.89 | 0.91 | 2.04 | 2.13 | 2.03 |
| -0.14 | 2.27 | 2.23 | 2.24 | 1.13 | 0.91 | 0.89 | 1.98 | 2.05 | 1.93 |
| 0.15 | 2.5 | 2.48 | 2.5 | 1.19 | 0.91 | 0.89 | 2.22 | 2.23 | 2.19 |

FIG. 16

| COX-2 | CTR | LPS 2μg/ml | LPS+ FL16μg/ml | LPS+ FL32μg/ml | LPS+ CUR5 μg/ml | LPS+CUR5+ FL16 μg/ml | LPS+CUR5+ FL32μg/ml | LPS+ CUR10μg/ml | LPS+CUR10+ FL16μg/ml | LPS+CUR10+ FL32μg/ml |
|---|---|---|---|---|---|---|---|---|---|---|
| | 0.13 | 2.93 | 2.83 | 2.95 | 3.03 | 3.01 | 2.96 | 2.33 | 2.23 | 2.24 |
| | 0.19 | 2.9 | 2.84 | 2.88 | 2.97 | 2.96 | 2.93 | 2.25 | 2.2 | 2.19 |
| | -0.11 | 2.51 | 2.52 | 2.5 | 2.68 | 2.65 | 2.58 | 1.91 | 1.82 | 1.8 |
| | -0.14 | 2.46 | 2.44 | 2.47 | 2.59 | 2.58 | 2.45 | 1.85 | 1.71 | 1.73 |
| | -0.19 | 2.51 | 2.49 | 2.5 | 2.69 | 2.69 | 2.62 | 1.98 | 1.83 | 1.85 |
| | 0.12 | 2.92 | 2.88 | 2.9 | 3.02 | 3.05 | 2.95 | 2.32 | 2.22 | 2.2 |

FIG. 17

5-LOX

| | CTR | LPS 2µg/ml | LPS+ FL16µg/ml | LPS+ FL32µg/ml | LPS+ CUR5 µg/ml | LPS+CUR5+ FL16 µg/ml | LPS+CUR5+ FL32µg/ml | LPS+ CUR10µg/ml | LPS+CUR10+ FL16µg/ml | LPS+CUR10+ FL32µg/ml |
|---|---|---|---|---|---|---|---|---|---|---|
| | 0.07 | 0.51 | 0.51 | 0.63 | 0.6 | 0.52 | 0.3 | 0.38 | 0.24 | 0.12 |
| | 0.06 | 0.55 | 0.56 | 0.6 | 0.58 | 0.51 | 0.32 | 0.37 | 0.21 | 0.11 |
| | -0.04 | 0.39 | 0.38 | 0.45 | 0.46 | 0.42 | 0.21 | 0.28 | 0.1 | 0.02 |
| | -0.11 | 0.35 | 0.34 | 0.36 | 0.37 | 0.32 | 0.16 | 0.21 | 0.04 | -0.05 |
| | -0.09 | 0.36 | 0.38 | 0.41 | 0.42 | 0.37 | 0.17 | 0.22 | 0.05 | -0.03 |
| | 0.11 | 0.55 | 0.57 | 0.58 | 0.63 | 0.55 | 0.36 | 0.41 | 0.34 | 0.18 |

FIG. 18

| IL-13 | LPS 2µg/ml | LPS+ FL16µg/ml | LPS+ FL32µg/ml | LPS+ CUR5 µg/ml | LPS+CUR5+ FL16 µg/ml | LPS+CUR5+ FL32µg/ml | LPS+ CUR10µg/ml | LPS+CUR10+ FL16µg/ml | LPS+CUR10+ FL32µg/ml |
|---|---|---|---|---|---|---|---|---|---|
| CTR 0.07 | -0.59 | -0.58 | -0.55 | 0.05 | 0.14 | 0.32 | 1.59 | 1.49 | 1.58 |
| 0.12 | -0.53 | -0.55 | -0.58 | 0.09 | 0.21 | 0.22 | 1.71 | 1.62 | 1.65 |
| -0.06 | -0.72 | -0.73 | -0.75 | -0.1 | 0.03 | 0.23 | 1.36 | 1.45 | 1.43 |
| -0.1 | -0.78 | -0.7 | -0.77 | -0.06 | 0.03 | 0.15 | 1.6 | 1.53 | 1.47 |
| -0.05 | -0.69 | -0.71 | -0.82 | 0.02 | 0.09 | 0.18 | 1.48 | 1.42 | 1.45 |
| 0.02 | -0.65 | -0.68 | -0.73 | -0.01 | 0.11 | 0.22 | 1.54 | 1.47 | 1.48 |

FIG. 19

THERAPEUTIC COMBINATIONS OF CURCUMINOIDS AND FLAVONOIDS

FIELD OF THE INVENTION

The present invention relates to inflammation, and novel combinations of active ingredients useful and synergistic for affecting the metabolic processes that underlie inflammatory processes and thereby treating or preventing inflammation.

BACKGROUND OF THE INVENTION

It has been previously demonstrated that bacterial endotoxins or lipopolysaccharides (LPS) play an important role in the pathogenesis of rheumatoid arthritis (RA) in an in vitro model of human chondrocytes. For example, LPS physically interact with collagen type II in the extracellular matrix (ECM) and trigger cartilage inflammation and degeneration.

Flavonoids are a diverse class of compounds found in a large variety of plants and herbs that have shown some benefit on human health. For example, U.S. Patent Publication 2013/0210753 describes methods for treating muscular dystrophies using flavonoids.

Baicalin and catechin are two types of flavonoids. Baicalin and catechin together act as a dual inhibitor of cyclooxygenase (COX) and 5-lipoxygenase (LOX), down-regulating gene and protein expression of several inflammatory mediators, possessing antioxidant effects and exerting beneficial effects in both in vitro and in vivo experimental models. Baicalin and catechin are the principal active ingredients in Limbrel, a medical food marketed by Primus Pharmaceuticals, Inc., Scottsdale Ariz., for the management of metabolic processes that underlie osteoarthritis. Limbrel® is supplied as an oral capsule, and contains from 250 to 500 mg of baicalin and catechin combined, for administration once or twice daily.

Curcuminoids are a class of potent anti-inflammatory phytochemicals which modulate the activation of NF-κB by inhibiting upstream kinases. Examples include curcumin, demethoxycurcumin, and bisdemethoxycurcumin. Previously, curcumin has been demonstrated to have a protective role on IL-1β induced Cox-2, VEGF, MMP-3 and MMP-9 in chondrocytes. Curcumin has been approved as a food additive by the United States Food and Drug Administration (FDA).

The aim of this work was to investigate the effects of curcuminoids and flavonoids on articular chondrocytes in vitro, and to develop a method and formulation that can effectively modulate the metabolic processes that underlie inflammatory conditions, and thereby treat inflammation.

SUMMARY OF THE INVENTION

It has surprisingly been discovered that the combination of curcuminoids and flavonoids is synergistically effective at modulating the metabolic processes that underlie inflammation, particularly in a chondrocyte inflammatory phenotype triggered by bacterial endotoxins or LPS, and that the combination can be used in the treatment of numerous diseases in which inflammation is involved, including osteoarthritis and rheumatoid arthritis. Based on this discovery, numerous products and methods of nutritional support and medical treatment are now possible.

One aspect of the present invention relates to a formulation or unit dosage form for affecting the metabolic processes that underlie inflammation. The formulation or unit dosage form includes nutritionally or therapeutically effective amounts of a curcuminoid and two flavonoids, preferably baicalin and catechin.

Another aspect of the present invention relates to a method of treating inflammation or managing inflammatory processes in a human being in need thereof. The method includes administering to the human being a formulation or unit dosage form comprising nutritionally or therapeutically effective amounts of a curcuminoid and two flavonoids, preferably baicalin and catechin.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The following detailed description of the invention is better understood when read in conjunction with the appended drawings. The figures show exemplary embodiments, but the subject matter is not limited to the specific elements and instrumentalities disclosed.

FIGS. 10-19 illustrate data used for plotting the graphs illustrated in FIGS. 1A-9.

DETAILED DESCRIPTION OF THE INVENTION

1. Definitions and Use of Terms

Figure 1A:
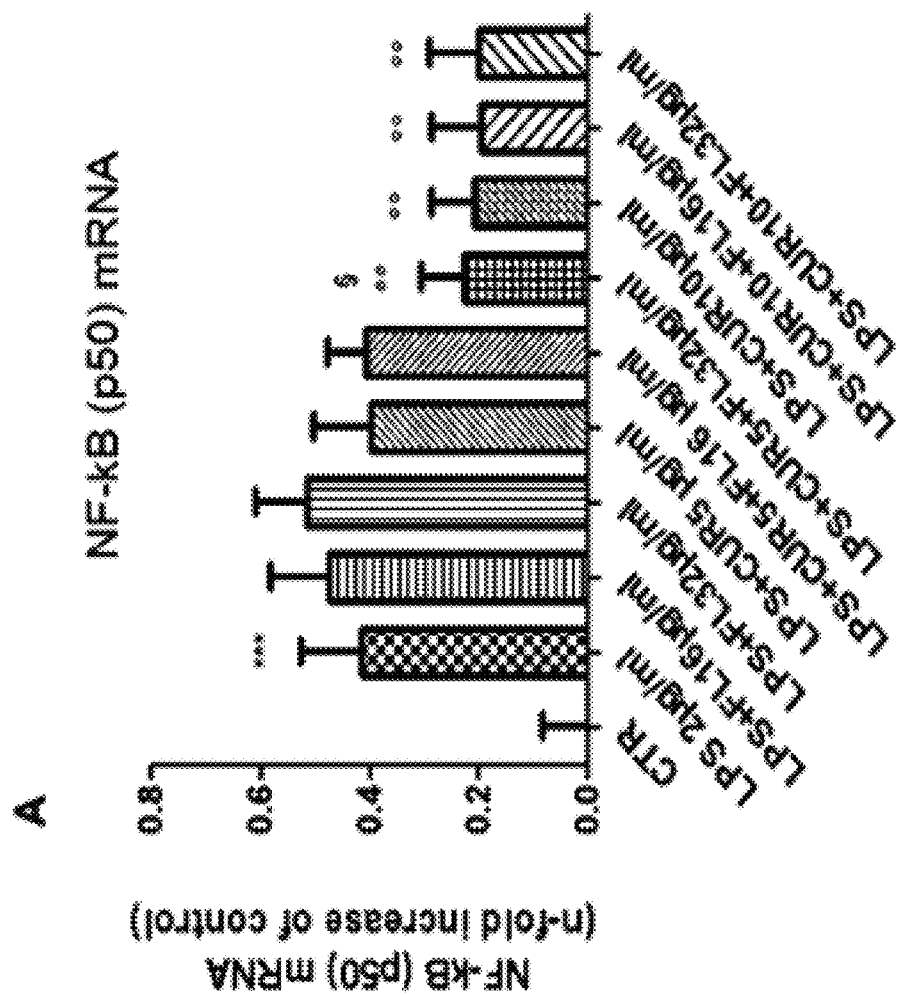
FIG. 1A is a graph showing the effects of curcumin and flavonoids at different concentrations on chondrocytes stimulated for 4 hours with LPS 2 μgm/1 on NF-kB (p50) mRNA expression.

As used in this specification and in the claims, which follow, the singular forms "a," "an" and "the" include plural referents unless the context clearly dictates otherwise.

"Therapeutically effective amount" or "nutritionally effective amount" means that amount which, when administered to an animal for supporting or affecting a metabolic process, or for treating or preventing a disease, is sufficient to effect such treatment or prevention of the disease, or supporting or affecting the metabolic process.

When ranges are given by specifying the lower end of a range separately from the upper end of the range, or specifying particular numerical values, it will be understood that a range can be defined by selectively combining any of the lower end variables, upper end variables, and particular numerical values that is mathematically possible.

When used herein the term "about" will compensate for variability allowed for in the dietary supplement, food and pharmaceutical industries and inherent in products in these industries, such as differences in product strength due to manufacturing variation and time-induced product degradation. The term allows for any variation, which in the practice of good manufacturing practices, would allow the product being evaluated to be considered equivalent in humans to the recited strength of a claimed product.

In the context of the present invention insofar as it relates to any of the disease conditions recited herein, the term "treatment" means to reduce the occurrence of a symptom or condition, or to relieve or alleviate at least one symptom associated with such condition, or to slow or reverse the progression of such condition, or to manage or affect the metabolic processes underlying such condition. Within the meaning of the present invention, the terms also denote to arrest, delay the onset (i.e., the period prior to clinical manifestation of a disease) and/or reduce the risk of developing or worsening a disease.

The phrase "acceptable" as used in connection with compositions of the invention, refers to molecular entities and other ingredients of such compositions that are physiologically tolerable and do not typically produce untoward reactions when administered to a subject (e.g., a mammal such as a human).

As used herein, the term "subject" refers to any mammal. In a preferred embodiment, the subject is human.

Throughout the description and claims of this specification, the word "comprise" and variations of the word, such as "comprising" and "comprises," means "including but not limited to," and is not intended to exclude, for example, other additives, components, integers or steps.

The term "curcuminoid" refers to curcumin and related phytochemicals that modulate the activation of NF-κB by inhibiting upstream kinases and possess potent anti-inflammatory activity. Structurally, a curcuminoid is a linear diarylheptanoid, with molecules such as curcumin or derivatives of curcumin with different chemical groups that have been formed to increase solubility or make them suitable for drug formulation. Exemplary curcuminoids include curcumin, demethoxycurcumin and bisdemethoxycurcumin, whose chemical structures are given below.

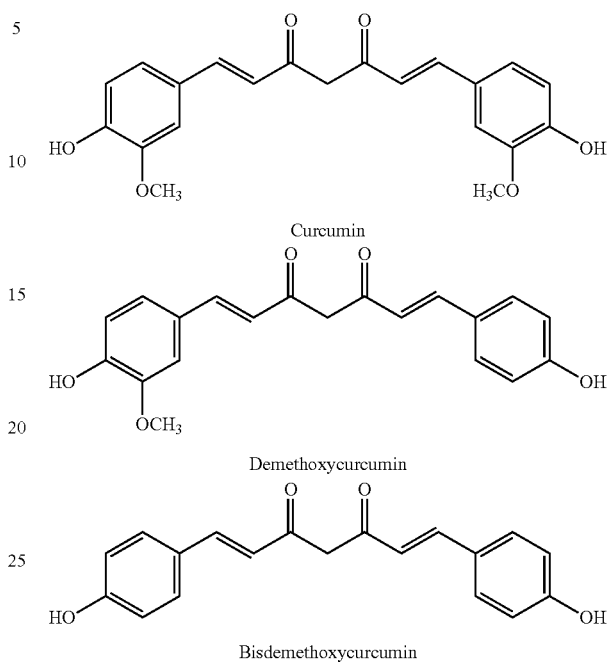

2. Formulations and Methods

The present invention relates to a formulation or unit dosage form for affecting the metabolic processes underlying inflammation, or treating inflammatory conditions, by reducing chondrocyte inflammatory phenotype triggered by LPS, reducing pro-inflammatory pathways, inhibiting LPS-induced genes involved in the inflammatory pathway and cartilage degradation processes, or suppressing LPS-induced upregulation of catabolic enzymes that mediate ECM cartilage degradation.

The formulation or unit dosage form may include a curcuminoid and flavonoids that achieve an antioxidant effect, an anti-inflammatory effect, or a combination of both effects.

The formulation includes a curcuminoid and one or more flavonoids, preferably curcumin, baicalin and catechin. Curcuminoids and flavonoids may act as an anti-inflammatory agent. Such composition may have a potent synergistic effect on reducing LPS-induced genes in articular chondrocytes in vitro.

Each active ingredient in the composition may be present in a different dose. An effective amount of the curcuminoid typically ranges from about 100 to about 1500 mg/day, from about 200 to about 1200 mg/day, or from about 300 to about 800 mg/day, preferably about 500 mg/day.

A single dosage form will commonly contain from about 100 to about 800 mg, from about 400 to about 600 mg, from about 100 to about 300 mg, from about 300 to about 500 mg, or from about 500 to about 800 mg of curcuminoids.

The flavonoids such as baicalin and catechin are typically evaluated as a combination. An effective amount of this combination typically ranges from about 10 to about 1500 mg/day. In one example, this combination may have, but is not limited to, any one of the following ranges: from about 10 to about 1000 mg/day, from about 100 to about 500 mg/day, from about 500 to about 900 mg/day, from about 200 to about 400 mg/day, from about 600 to about 800 mg/day, from about 300 to about 700 mg/day, and from about 200 to about 1000 mg/day.

The combined amount of baicalin and catechin in a unitary dosage form will typically range from 100 to 800 mg, but preferably ranged from 200 to 300 mg or from 400 to 600 mg, most preferably 250 mg or 500 mg. The ratio of baicalin to catechin may be, but not limited to, any one of the following ratios: from about 10:1 to about 1:10, from about 10:1 to about 2:1, from about 1:2 to about 1:10, from about 1:5 to about 5:1, and from about 90:10 to about 10:90. In one example, the ratio of baicalin to catechin may be from about 8:1 to about 1:2. In all the embodiments of the present invention, the catechin is preferably present as (+)-catechin.

The foregoing doses can be administered in any dosing regimen, including once or twice daily. When administered twice daily, one half of the daily dose will preferably be administered with each dose.

In one embodiment, the composition may suppress LPS induced gene expression, including but not limited to, NF-κB, MMP-1β, MMP-3, MMP-9, MMP-13, COX-2 and 5-LOX mRNA expression. The composition may also increase anti-inflammatory IL-13 cytokine that is otherwise reduced by LPS.

According to one aspect of the present technology, a method of treating inflammation (or affecting the metabolic processes underlying inflammation) may include providing a pharmaceutical composition comprising an effective amount of curcumin and flavonoids, and administering the composition to a subject, preferably a human being. The flavonoids preferably include baicalin and catechin.

A pharmaceutical composition is formulated to be compatible with its intended route of administration. Examples of suitable routes of administration include parenteral, oral, transmucosal, and rectal administration. The compounds for use in the method of the invention can be formulated for administration by any suitable route, such as for oral or parenteral, for example, transmucosal (e.g., sublingual, lingual, (trans)buccal), nasal, (trans)dermal, and (trans)rectal administration.

Suitable compositions and dosage forms include tablets, capsules, caplets, pills, gel caps, troches, dispersions, suspensions, solutions, syrups, granules, beads, gels, powders, pellets, magmas, lozenges, discs, suppositories, liquid sprays, or dry powders.

It is preferred that the compounds are orally administered. Suitable oral dosage forms include, for example, tablets, capsules or caplets prepared by conventional means with acceptable excipients such as binding agents (e.g., polyvinylpyrrolidone or hydroxypropylmethylcellulose); fillers (e.g., lactose, microcrystalline cellulose or calcium phosphate); lubricants (e.g., magnesium stearate, talc or silica); disintegrates (e.g., sodium starch glycolate); or wetting agents (e.g., sodium lauryl sulphate).

If desired, the tablets can be coated, e.g., to provide for ease of swallowing or to provide a delayed release of active, using suitable methods. Liquid preparation for oral administration can be in the form of solutions, syrups or suspensions. Liquid preparations (e.g., solutions, suspensions and syrups) are also suitable for oral administration and can be prepared by conventional means with acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

3. Experiments Conducted

Various experiments were conducted to determine effects of various active ingredients on articular chondrocytes in vitro.

3.1 Cell Cultures and Treatments

Human articular chondrocytes were cultured in six well culture Petri dishes at a density of $2.5 \times 10^5$ cells/well, in a specific chondrocyte growth medium supplemented with 1% antibiotic-antimycotic mixture, at 37° C. in 5% $CO_2$ humidified incubator. The medium was renewed every 2 days. Sixteen hours after planting (time 0), chondrocytes were stimulated with LPS (2 μg/ml; Escherichia coli serotype 055:B5) alone or in combination with different treatments: flavonoids of various concentrations including 16 μg/ml and 32 μg/ml, curcumin of various concentrations including 5 μg/ml and 10 μg/ml, or drug combinations for 4 hours. Finally, the cells and medium underwent molecular evaluation 4 hours after the treatments.

3.2 RNA Isolation, cDNA Synthesis, and Real-Time Quantitative PCR Amplification

Total RNA was isolated from human chondrocytes for reverse-PCR real time evaluation of IL-1beta, COX2, MMP1, MMP9, MMP13, NF-kB (p50), NF-kB (p65), IL-13 and 5-LOX mRNA (Real Time PCR system, mod 7500, Applied Biosystems, Carlsbad, Calif.) using Trizol Reagent Kit (Life Technologies, Monza, Italy). The first strand of cDNA was synthesized from 5.0 μg total RNA using a high capacity cDNA Archive kit (Applied Biosystems, Carlsbad, Calif.). β-actin mRNA was used as an endogenous control to allow the relative quantification. PCR Real Time was performed on both targets and endogenous controls using SYBR Premix DimerEraser (Perfect Real Time). The amplified PCR products were quantified by measuring the calculated cycle thresholds (CT) of IL-1beta, COX2, MMP1, MMP9, MMP13, NF-kB (p50), NF-kB (p65), IL-13 and 5-LOX and β-Actin mRNA. The amounts of specific mRNA in samples were calculated using the $2^{\Delta\Delta CT}$ method. The mean value of normal chondrocytes target levels became the calibrator and the results are expressed as the n-fold difference relative to normal controls (relative expression levels).

3.3 Statistical Analysis

Data are expressed as means±S.D. of no less than six experiments for each test. Statistical analysis was performed by one-way analysis of variance (ANOVA) followed by the Student-Newman Keuls test. The statistical significance of differences was set at $p<0.05$. All graphs are presented using GraphPad Prism 5 (GraphPad Software, Inc. La Jolla, Calif., USA).

3.4 Experimental Results

Human chondrocytes were stimulated with 2 μg/ml of LPS and co-treated with one or more various compounds at different concentrations for four hours to determine their anti-inflammatory effects as well any potential synergistic effects. For example, compounds include any one of the following or the combination thereof: different doses of flavonoids at various concentrations such as 16 and 32 μg/ml and curcumin at various concentrations such as 5 and 10 μg/ml. The curcumin and flavonoid doses were chosen after preliminary experiments on human chondrocyte viability using the MTT assay (data not shown).

3.4.1 Synergistic Effect of Flavonoids and Curcumin on NF-κB mRNA Expression In a first example, the effects of flavonoids and curcumin on LPS induced transcription factor NF-κB pathway in human articular chondrocytes were studied. NF-κB stimulates the expression of different genes that amplify the inflammatory process and are involved in the pathogenesis and progression of osteoarthritis and rheumatoid arthritis.

Figure 1B:
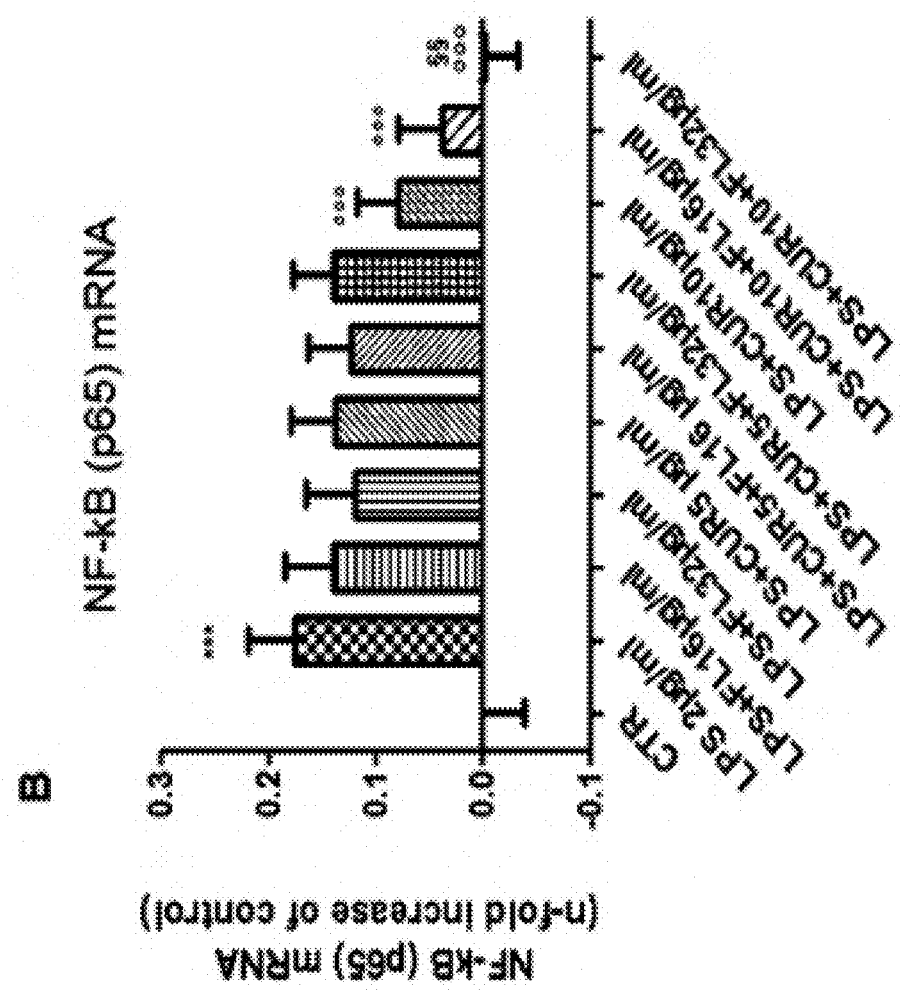
FIG. 1B is a graph showing the effects of curcumin and flavonoids at different concentrations on chondrocytes stimulated for 4 hours with LPS 2 μgm/1 on NF-kB (p65) mRNA expression.

FIGS. 1A-1B illustrate the level of NF-κB expression under the influence of different compounds, such as curcumin, denoted by "CUR," and flavonoids denoted by "FL" in the figures. FIG. 1A relates to NF-κB associated with p50 phosphorylation, whereas FIG. 1B relates to NF-κB associated with p65 phosphorylation. As illustrated in FIGS. 1A-1B, control chondrocytes, denoted by "CTR," had a very low basal NF-κB expression. As also shown in these figures, LPS induced a significant expression of NF-κB. As illustrated in these figures, treatment of chondrocytes with flavonoids of various concentrations such as 16 μg/ml and 32 μg/ml for 4 hours did not result in any change in either NF-κB p50 or NF-κB p65 expressions. Likewise, curcumin of 5 μg/ml also failed to result in any change in either NF-κB p50 or NF-κB p65 expressions.

On the other hand, referring to FIG. 1A, 32 μg/ml flavonoids and 5 μg/ml curcumin in combination produced a significant reduction of NF-κB p50 level, despite the fact that the single dose of either compound did not exert any significant change.

Further, as shown in FIGS. 1A-1B, 10 μg/ml of curcumin alone or in association with flavonoids such as 16 μg/ml and 32 μg/ml also produced a more pronounced decrease of both NF-kB p50 and p65.

Referring to FIG. 1B, even though the single dose of flavonoid at 32 μg/ml was ineffective in decreasing NF-κB p65, its combination with curcumin 10 μg/ml abolished NF-κB p65 expression. This effect was significant greater than that caused by curcumin 10 μg/ml alone, thus suggesting a synergistic effect.

All the above findings suggest a synergy between these flavonoids and curcumin.

In FIGS. 1A-1B, data are presented as mean+S.D. of six experiments and are expressed as the n-fold increase with respect to the control. ***$p<0.001$ versus control(CTR), °°°$p<0.001$ versus LPS, $^§$ $p<0.01$ versus LPS+CUR5 and versus LPS+FL32, and $^{§§}$ $p<0.01$ versus LPS+CUR10 and versus LPS+FL32.

3.4.2 Synergistic Effect of Flavonoids and Curcumin on IL-1β mRNA Expression In a second example, the effects of flavonoids and curcumin on LPS induced IL-1β mRNA in human articular chondrocytes were studied. IL-1β is a pro-inflammatory cytokine that plays a key role in cartilage degradation. IL-1β mRNA was not present in untreated human chondrocytes, but LPS incubation of chondrocytes for 4 hours induced a marked increase of IL-1β message as shown in FIG. 2.

Figure 2:
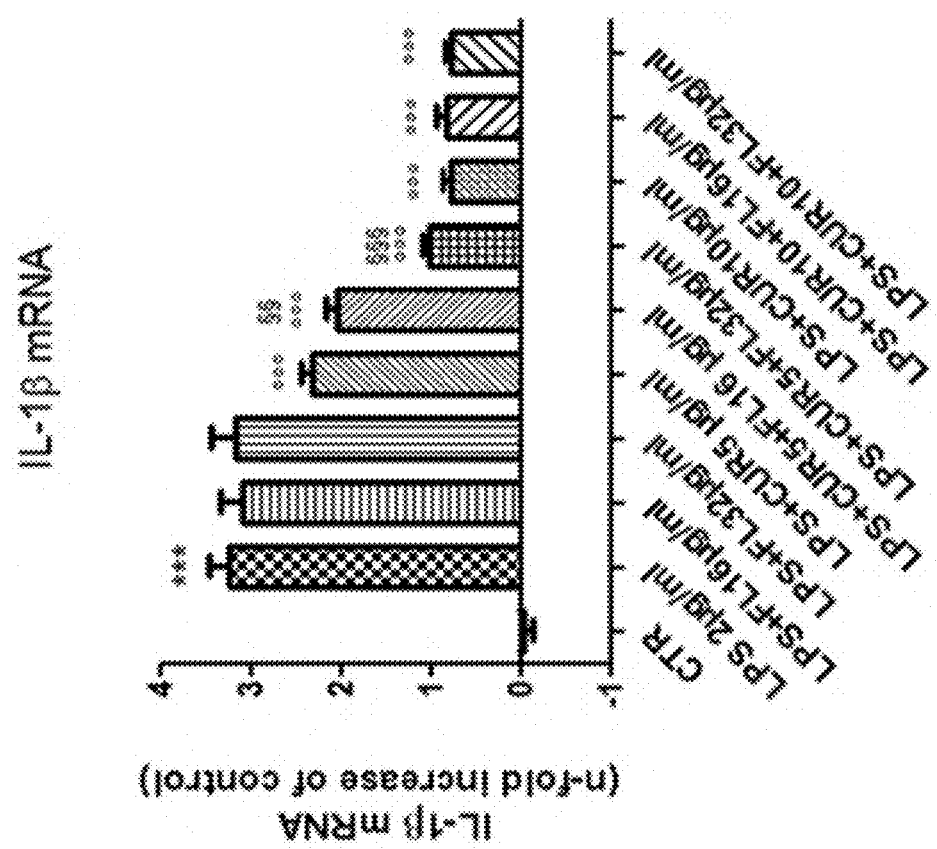
FIG. 2 is a graph showing the effects of curcumin and flavonoids at different concentrations on chondrocytes stimulated for 4 hours with LPS on IL-1β mRNA expression.

As shown in FIG. 2, treatment of chondrocytes with curcumin at the dose of 5 μg/ml for 4 hours significantly blunted IL-1β message. Furthermore, the simultaneous incubation with flavonoids, at either 16 or 32 μg/ml, and curcumin 5 μg/ml reduced significantly and in a dose-dependent manner IL-1β mRNA. As a result, the combining effect of flavonoids and curcumin inhibited the gene level more than each compound alone. The above findings suggest a synergistic effect between flavonoids and curcumin. FIG. 2 also shows that treatment with either 10 μg/ml curcumin alone or in combination with both doses of flavonoids further decreased the cytokine expression in human chondrocytes.

In FIG. 2, data are presented as mean+S.D. of six experiments and are expressed as the n-fold increase with respect to the control. ***$p<0.001$ versus control ("CTR"), °°°$p<0.001$ versus LPS, $^{§§}$ $p<0.01$ versus LPS+CUR5 and versus LPS+FL16, and $^{§§§}$ $p<0.001$ versus LPS+CUR5 and versus LPS+FL32.

3.4.3 Synergistic Effect of Flavonoids and Curcumin on MMPs mRNA Expression

In a third example, the effects of flavonoids and curcumin on LPS induced matrix-degrading metalloproteinases (MMPs) in human articular chondrocytes were studied. Inflammatory cytokines are involved in cartilage degeneration, and induce the release of MMPs by articular chondrocytes. Various MMPs were studied, including MMP-1, MMP-3, MMP-9 and MMP-13. Results of each MMP are shown in FIGS. 3-6, respectively.

Figure 3:
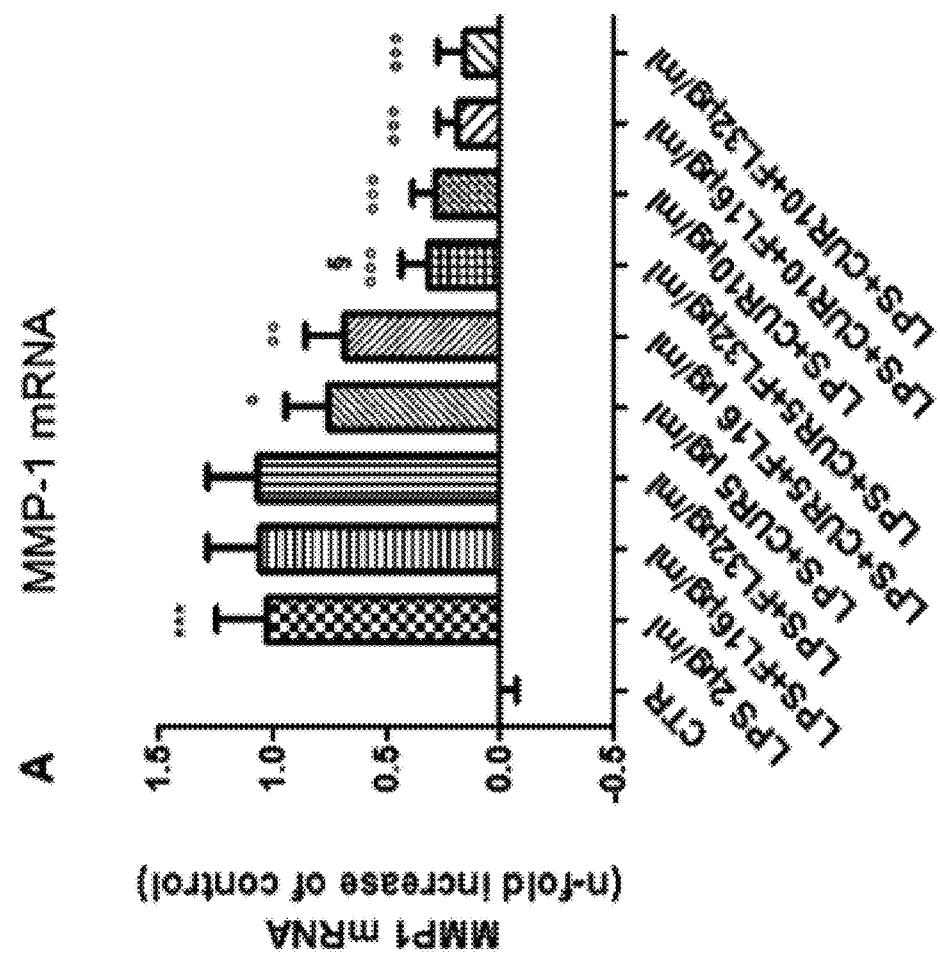
FIG. 3 is a graph showing the effects of curcumin and flavonoids at different concentrations on chondrocytes stimulated for 4 hours with LPS on MMP-1 mRNA expression.

FIG. 3 illustrates the level of MMP-1 under the influence of different compounds. As illustrated in FIG. 3, control chondrocytes, denoted by "CTR," had a very low level of MMP-1, but LPS stimulation resulted in an increase in MMP-1. As shown in FIG. 3, the expression of MMP-1 was significantly reduced by treatment with 5 μg/ml curcumin alone or in association with flavonoids, where flavonoids were concentrated at either 16 μg/ml or 32 μg/ml. As also shown in FIG. 3, the higher curcumin dose, e.g., 10 μg/ml, and co-incubation with flavonoids resulted in an additional decrease in a concentration-dependent manner. Moreover, the combination of 32 μg/ml flavonoids and 5 μg/ml curcumin caused a greater decrease in MMP-1 expression with respect to curcumin alone. The above findings suggest a synergistic effect between flavonoids and curcumin.

Figure 4:
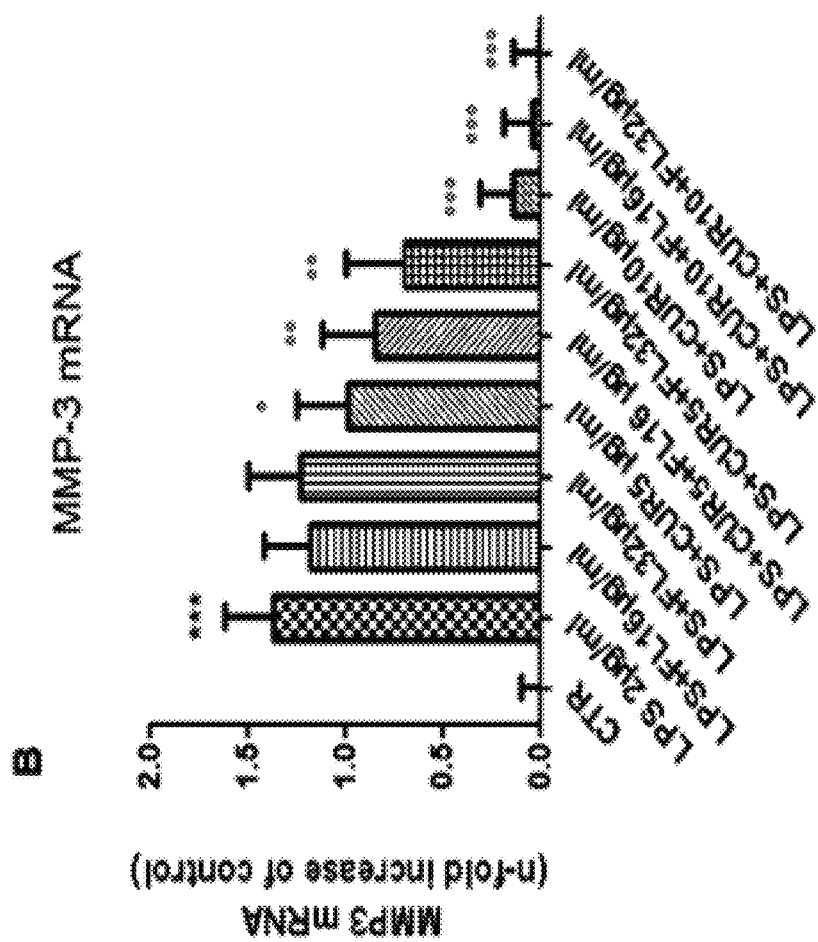
FIG. 4 is a graph showing the effects of curcumin and flavonoids at different concentrations on chondrocytes stimulated for 4 hours with LPS on MMP-3 mRNA expression.

FIG. 4 illustrates the level of MMP-3 under the influence of different compounds. As illustrated in FIG. 4, control chondrocytes, denoted by "CTR," had a very low level of MMP-3, but LPS stimulation resulted in an increase in MMP-3. As shown in FIG. 4, the expression of MMP-3 was significantly reduced by treatment with 5 μg/ml curcumin alone or in association with flavonoids, where flavonoids were concentrated at either 16 μg/ml or 32 μg/ml. As also shown in FIG. 4, the higher curcumin dose, e.g., 10 μg/ml, and co-incubation with flavonoids resulted in an additional decrease in a concentration-dependent manner. The above findings suggest a synergistic effect between flavonoids and curcumin.

In both FIGS. 3 and 4, data are presented as mean+S.D. of six experiments and are expressed as the n-fold increase with respect to the control. ***$p<0.001$ versus control (CTR), °°°$p<0.001$ versus LPS 2 μg, °°$p<0.01$ versus LPS; °$p<0.05$ versus LPS, $^§$ $p<0.01$ versus LPS+CUR5 and versus LPS+FL32.

Figure 5:
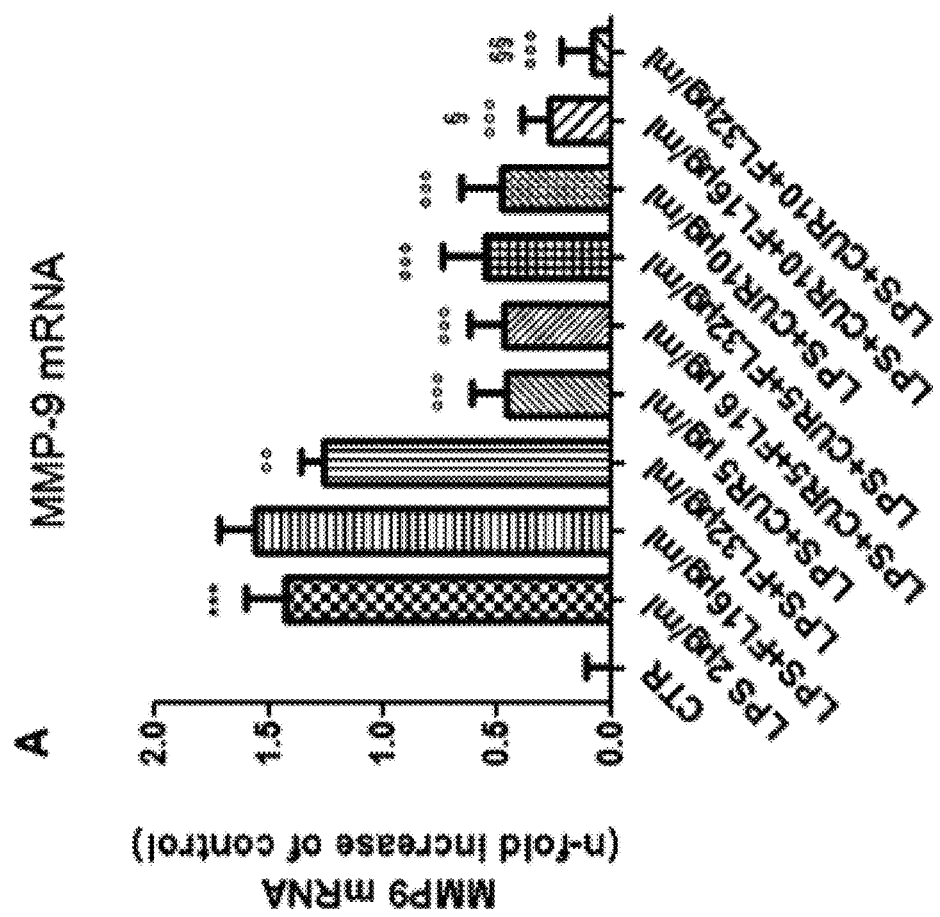
FIG. 5 is a graph showing the effects of curcumin and flavonoids at different concentration on chondrocytes stimulated for 4 hours with LPS on MMP-9 mRNA expression.

FIG. 5 illustrates the level of MMP-9 under the influence of different compounds. As illustrated in FIG. 5, control chondrocytes, denoted by "CTR," had a very low level of MMP-9, but LPS stimulation resulted in an increase in MMP-9. As shown in FIG. 5, LPS induced MMP-9 expression was significantly decreased by treatment with flavonoids alone at the dose of 32 ng/ml. MMP-9 was also decreased by treatment with flavonoids at 32 ng/ml and with curcumin at either 5 or 10 μg/ml. As also shown in FIG. 5, treatment of chondrocytes with 10 ng/ml of curcumin in association with flavonoids at either 16 µg/ml or 32 ng/ml caused a significant and dose-dependent decrease that was higher than curcumin alone. The above findings suggest a synergistic effect between flavonoids and curcumin. In FIG. 5, data are presented as mean+S.D. of six experiments and are expressed as the n-fold increase with respect to the control. ***p<0.001 versus control (CTR), °°°p<0.001 versus LPS, °°p<0.01 versus LPS, § p<0.05 versus LPS+CUR10 and versus LPS+FL16, §§§ p<0.001 versus LPS+CUR10 and versus LPS+FL32.

Figure 6:
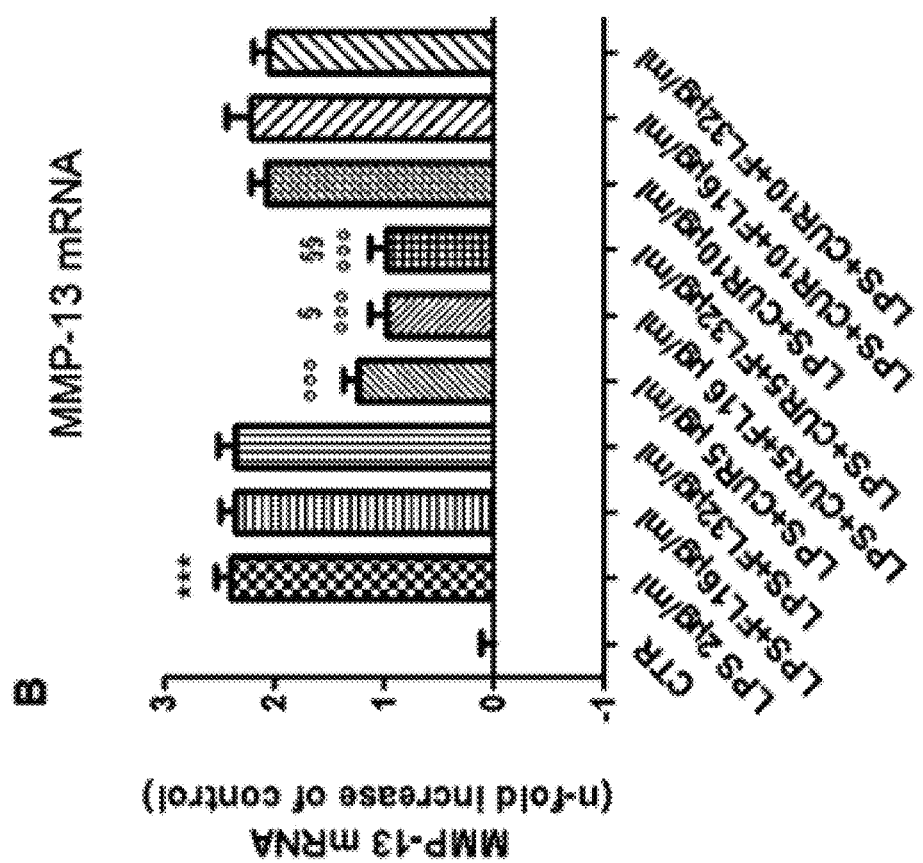
FIG. 6 is a graph showing the effects of curcumin and flavonoids at different concentration on chondrocytes stimulated for 4 hours with LPS on MMP-13 mRNA expression.

FIG. 6 illustrates the level of MMP-13 under the influence of different compounds. As illustrated in FIG. 6, control chondrocytes, denoted by "CTR," had a very low level of MMP-13, but LPS stimulation resulted in an increase in MMP-13. As shown in FIG. 6, the effects of combining curcumin 5 ng/ml with flavonoids at either 16 ng/ml or 32 ng/ml markedly suppressed MMP-13 gene level in chondrocytes. FIG. 6 shows that MMP-13 reduction was more pronounced than obtained by curcumin alone. The above findings suggest the synergistic effect of flavonoids and curcumin. In FIG. 6, data are presented as mean+S.D. of six experiments and are expressed as the n-fold increase with respect to the control. ***p<0.001 versus control (CTR), °°°p<0.001 versus LPS, °°p<0.01 versus LPS, § p<0.05 versus LPS+CUR5 and versus LPS+FL16, and §§ p<0.01 versus LPS+CUR5 and versus LPS+FL32.

3.4.4 Synergistic Effect of Flavonoids and Curcumin on COX-2 mRNA Expressions In a fourth example, the effects of flavonoids and curcumin on LPS induced cyclooxygenase-2 (COX-2) in human articular chondrocytes were studied. Inflammatory cytokines are involved in cartilage degeneration. Proinflammatory enzymes are involved in osteoarthritis and rheumatoid arthritis processes. LPS activates COX-2.

Figure 7:
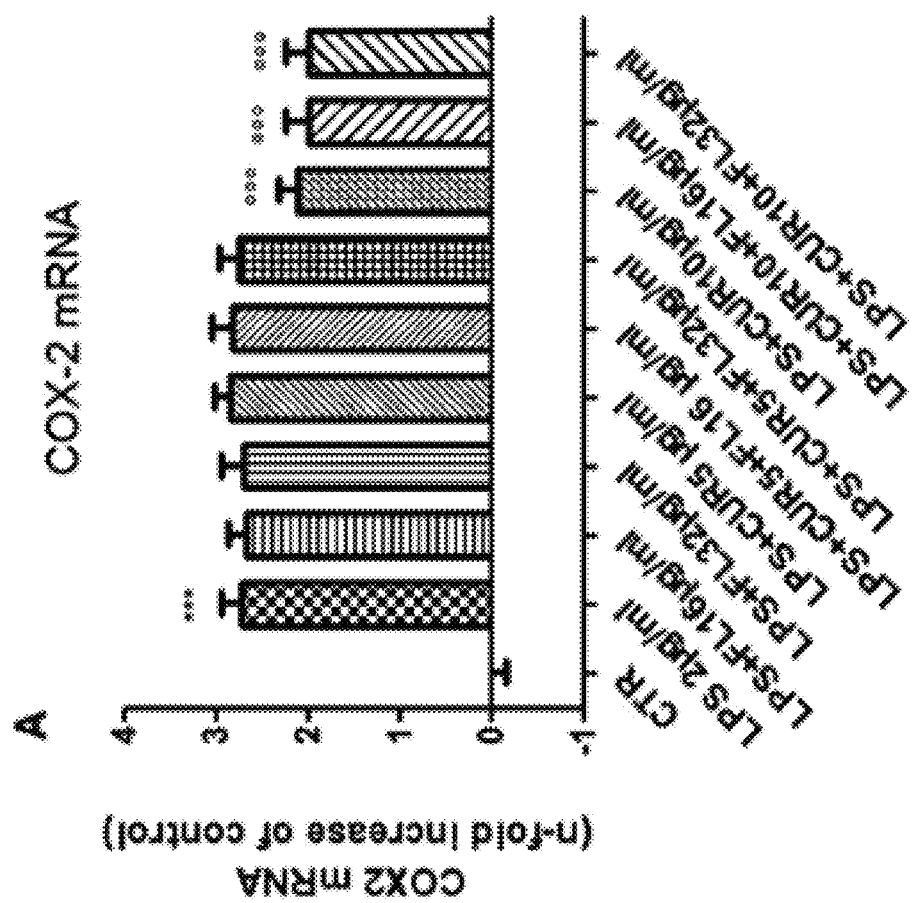
FIG. 7 is a graph showing the effects of curcumin and flavonoids at different concentrations on chondrocytes stimulated for 4 hours with LPS on COX-2 mRNA expression.

As illustrated in FIG. 7, control chondrocytes, denoted by "CTR," had a very low level of COX-2, but LPS stimulation resulted in an increase in COX-2. FIG. 7 illustrates that the enhanced COX-2 mRNA level was significantly reduced by treatment with 10 µg/ml curcumin alone or in combination with flavonoids, at either 16 µg/ml or 32 µg/ml.

In FIG. 7, data are presented as mean+S.D. of six experiments and are expressed as the n-fold increase with respect to the control. ***p<0.001 versus control (CTR), °°°p<0.001 versus LPS, °°p<0.01 versus LPS, °p<0.05 versus LPS, § p<0.05 versus LPS+CUR10 and versus LPS+FL16, §§ p<0.01 versus LPS+CUR5 and versus LPS+FL32, and §§§ p<0.001 versus LPS+CUR10 and versus LPS+FL32.

3.4.5 Synergistic Effect of Flavonoids and Curcumin on 5-LOX mRNA Expressions In a fifth example, the effects of flavonoids and curcumin on LPS induced 5-lipoxygenase (LOX) in human articular chondrocytes were studied. Inflammatory cytokines are involved in cartilage degeneration. Proinflammatory enzymes are involved in osteoarthritis and rheumatoid arthritis processes. LPS activates 5-LOX.

Figure 8:
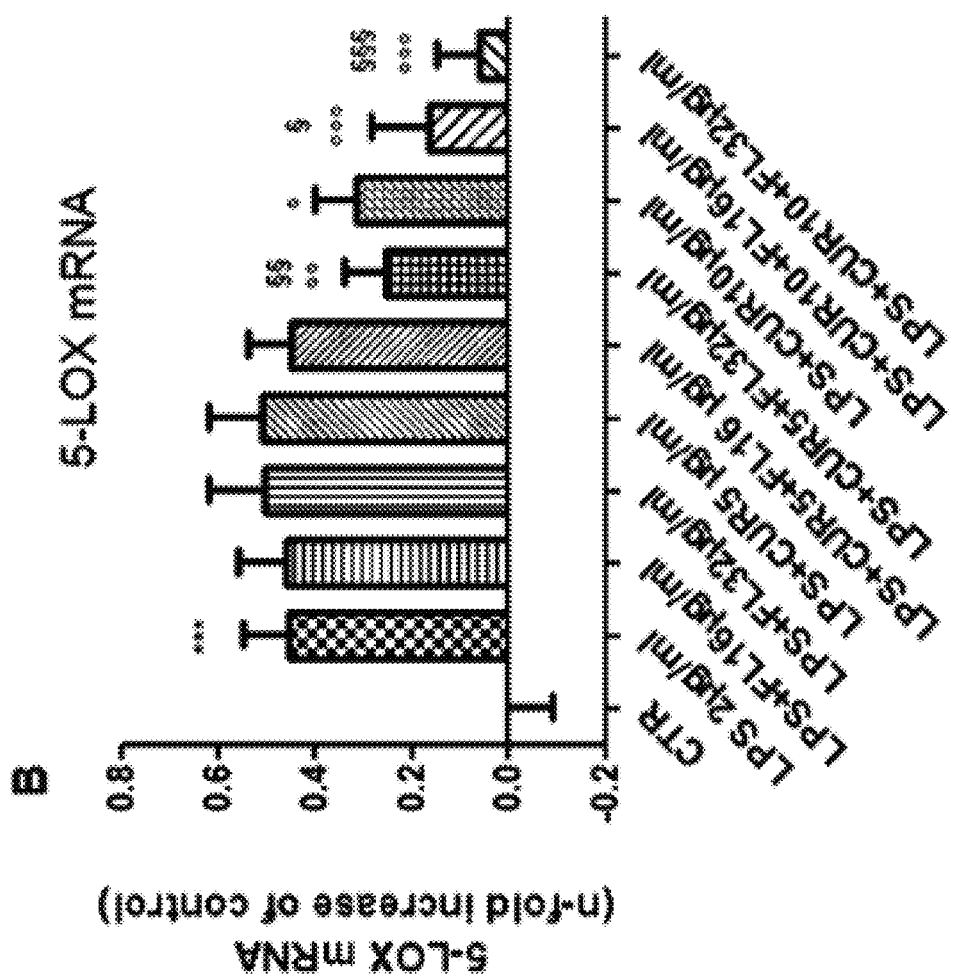
FIG. 8 is a graph showing the effects of curcumin and flavonoids at different concentrations on chondrocytes stimulated for 4 hours with LPS on 5-LOX mRNA expression.

As illustrated in FIG. 8, control chondrocytes, denoted by "CTR," had a very low level of 5-LOX, but LPS stimulation resulted in an increase in 5-LOX. FIG. 8 illustrates that treatment with 32 µg/ml of flavonoids in association with 5 µg/ml of curcumin significantly limited the LPS induced increase of 5-LOX enzyme compared to single treatment of either compounds. Similarly, 10 µg/ml of curcumin blunted 5-LOX level, but the effect of both doses of flavonoids in combination with 10 µg/ml of curcumin was higher than that of the single treatment, and dose-dependent. These findings suggest the synergistic effect of flavonoids and curcumin.

In FIG. 8, data are presented as mean+S.D. of six experiments and are expressed as the n-fold increase with respect to the control. ***p<0.001 versus control (CTR), °°°p<0.001 versus LPS, °°p<0.01 versus LPS, °p<0.05 versus LPS, § p<0.05 versus LPS+CUR10 and versus LPS+FL16, §§ p<0.01 versus LPS+CUR5 and versus LPS+FL32, §§§ p<0.001 versus LPS+CUR10 and versus LPS+FL32.

3.4.6 Synergistic Effect of Flavonoids and Curcumin on IL-13 mRNA Expressions In a sixth example, the effects of flavonoids and curcumin on LPS induced IL-13 mRNA in human articular chondrocytes were studied. IL-13 is an anti-inflammatory and immunoregulatory cytokine.

Figure 9:
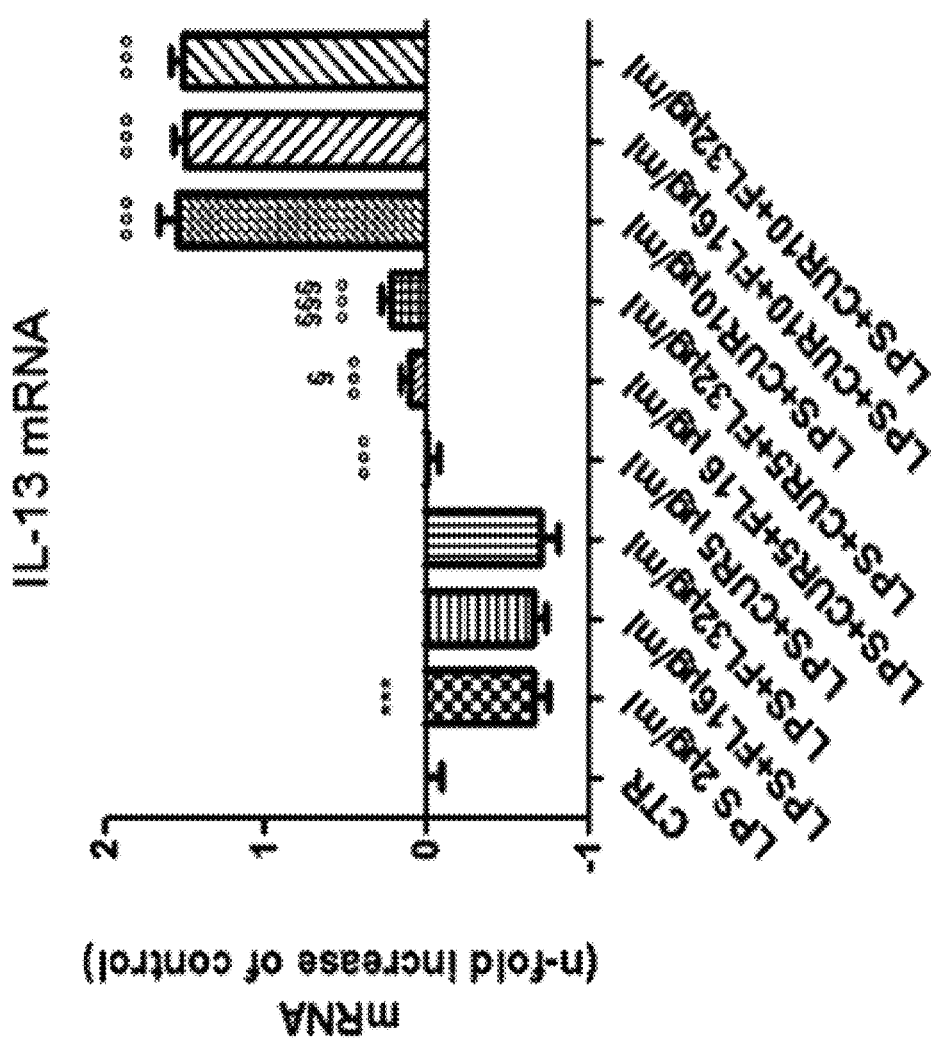
FIG. 9 is a graph showing the effects of curcumin and flavonoids at different concentrations on chondrocytes stimulated for 4 hours with LPS on IL-13 mRNA expression.
Figure 20:
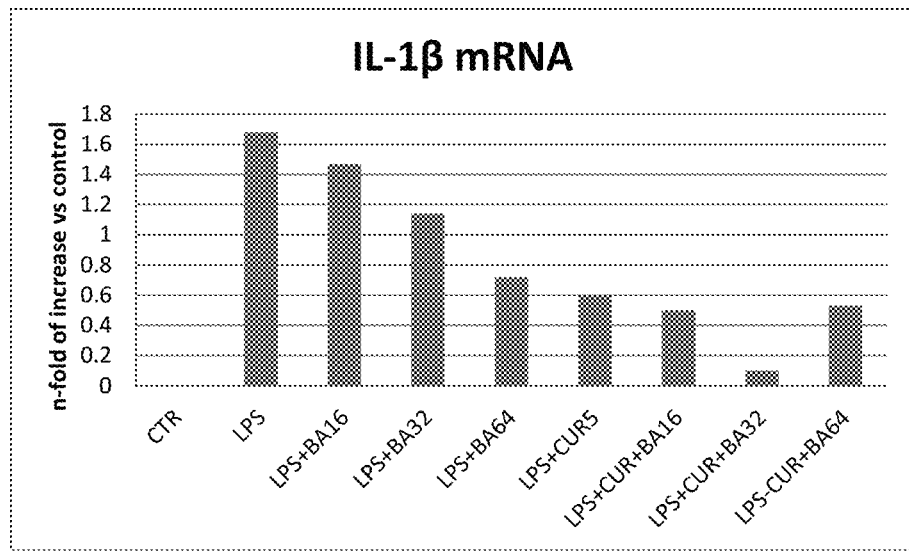
FIG. 20 is a bar graph illustrating the effects of curcumin (CUR 5 µg/ml), and baicalin (BA: 16 µg/ml, 32 µg/ml and 64 µg/ml) at different concentrations on chondrocytes stimulated for 4 h with LPSon IL-1beta mRNA expression.

As shown in FIG. 9, a very low level of IL-13 was found in control chondrocytes, and LPS induced a greater reduction of the gene. As shown in FIG. 9, curcumin alone, at either 5 µg/ml or 10 µg/ml, significantly increased in a dose dependent manner IL-13 level. Similarly, curcumin at either 5 or 10 µg/ml, and in association with flavonoids at either 16 µg/ml or 32 µg/ml significantly increased in a dose dependent manner IL-13 level. Moreover, the simultaneous incubation with 5 ng/ml of curcumin and flavonoids at either 16 µg/ml or 32 µg/ml significantly increased the expression of the cytokine in LPS stimulated chondrocytes. This combining effect was more effective than the single treatment. These findings suggest the synergistic effect of flavonoids and curcumin.

In FIG. 9, data are presented as mean+S.D. of six experiments and are expressed as the n-fold increase with respect to the control. ***p<0.001 versus control (CTR), °°°p<0.001 versus LPS, § p<0.05 versus LPS+CUR5 and versus LPS+FL16, §§§ p<0.001 versus LPS+CUR5 and versus LPS+FL32.

3.5 Experiment Data

FIGS. 10-19 illustrate data used for plotting graphs illustrated in FIGS. 1A-9. For example, FIG. 10 provides data obtained from the experiment involving NF-kB (p50) mRNA expression, the result of which is illustrated in FIG. 1A. FIG. 11 provides data obtained from the experiment involving NF-kB (p65) mRNA expression, the result of which is illustrated in FIG. 1B. FIG. 12 provides data obtained from the experiment involving IL-1β mRNA expression, the result of which is illustrated in FIG. 2. FIG. 13 provides data obtained from the experiment involving MMP-1 mRNA expression, the result of which is illustrated in FIG. 3. FIG. 14 provides data obtained from the experiment involving MMP-3 mRNA expression, the result of which is illustrated in FIG. 4. FIG. 15 provides data obtained from the experiment involving MMP-9 mRNA expression, the result of which is illustrated in FIG. 5. FIG. 16 provides data obtained from the experiment involving MMP-13 mRNA expression, the result of which is illustrated in FIG. 6. FIG. 17 provides data obtained from the experiment involving COX-2 mRNA expression, the result of which is illustrated in FIG. 7. FIG. 18 provides data obtained from the experiment involving 5-LOX mRNA expression, the result of which is illustrated in FIG. 8. FIG. 19 provides data obtained from the experiment involving IL-13 mRNA expression, the result of which is illustrated in FIG. 9.

3.6 Conclusion

The above experiments demonstrate that LPS in human articular chondrocytes upregulates the NF-κB pathway and triggers pro-inflammatory activity. Flavonoids alone, at doses of either 16 or 32 μg/ml, do not have significant effects on NF-κB pathway. Curcumin alone may or may not have significant effects on NF-κB pathway, depending on its particular dose. For example, cucumin at 5 μg/ml may not significantly affect NF-κB pathway, but curcumin at 10 μg/ml may have this effect. As shown in the above experiments, the combination of ineffective doses of flavonoids with ineffective doses of curcumin, e.g., 5 μg/ml, resulted in a significant reduction in the chondrocyte inflammatory phenotype triggered by LPS. Moreover the combination of ineffective doses of flavonoids with an effective dose of curcumin, e.g., 10 μg/ml, caused a greater reduction in the pro-inflammatory pathway than the single dose of curcumin. Accordingly, these experiments demonstrate that flavonoids and curcumin have synergistic effects on LPS induced inflammation in articular chondrocytes.

Furthermore, these experiments demonstrate that flavonoids with curcumin inhibited LPS-induced genes involved in the inflammatory pathway and cartilage degradation processes, and overexpressed a pro-repair cytokine in chondrocytes. In addition, flavonoids and curcumin suppressed LPS-induced upregulation of catabolic enzymes that mediate ECM cartilage degradation, including MMP-1, MMP-3, MMP-9, MMP-13, COX-2 and 5-LOX. These proteins are regulated by NF-κB, suggesting that the NF-κB is involved in LPS-induced cartilage degradation.

Furthermore, these experiments demonstrate that treatment with curcumin and flavonoids in association, suppressed NF-κB expression, reduced the expression of IL-1β, of MMP-1, MMP-3, MMP-9, and MMP-13 and modulated levels of IL-13, COX-2 and 5-LOX.

4. References

The entire disclosures of all publications mentioned herein are incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

(1) Lorenz W, Buhrmann C, Mobasheri A, Lueders C, Shakibaei M. Bacterial lipopolysaccharides form procollagen-endotoxin complexes that trigger cartilage inflammation and degeneration: implications for the development of rheumatoid arthritis. Arthritis Res Ther. 2013; 15(5):R111.

(2) Bitto A, Squadrito F, Irrera N, Pizzino G, Pallio G, Mecchio A, Galfo F, Altavilla D. Flavocoxid, a nutraceutical approach to blunt inflammatory conditions. Mediators Inflamm. 2014; 2014:790851.

(3) Burnett, B. P.; Bitto, A.; Altavilla, D.; Squadrito, F.; Levy, R. M.; Pillai, L. Flavocoxid inhibits phospholipase A2, peroxidase moieties of the cyclooxygenase (COX) and 5-lipoxygenase, modifies COX-2 gene expression and acts as an antioxidant. Mediators of Inflammation, 2011:385780. doi: 10.1155/2011/385780.

(4) Levy, R.; Khokhlov, A.; Kopenkin, S.; Bart, B.; Ermolova, T.; Kantemirova, R.; Mazurov, V.; Bell, M.; Caldron, P.; Pillai, L.; Burnett, B. Efficacy and safety of flavocoxid compared with naproxen in subjects with osteoarthritis of the knee—a subset analysis. Adv. Ther, 2010, 27(12), 953-962.

(5) Henrotin Y Henrotin Y, Clutterbuck A L, Allaway D, Lodwig E M, Harris P, Mathy-Hartert M, Shakibaei M, Mobasheri A. Biological actions of curcumin on articular chondrocytes. Osteoarthritis Cartilage. 2010 February; 18(2):141-149.

(6) Altavilla D, Squadrito F, Bitto A, Polito F, Burnett B P, Di Stefano V, Minutoli L. Flavocoxid, a dual inhibitor of cyclooxygenase and 5-lipoxygenase,blunts pro-inflammatory phenotype activation in endotoxin-stimulated macrophages. Br J Pharmacol. 2009 August; 157(8):1410-8.

(7) Livak, K. J. and T. D. Schmittgen, 2001. Analysis of relative gene expression data using real-time quantitative PCR and the 2(-Delta Delta C(T)) Method. Methods 25:402-408.

(8) Tsuchida A I, Beekhuizen M, 't Hart M C, Radstake T R, Dhert W J, Saris D B, van Osch G J, Creemers L B. Cytokine profiles in the joint depend on pathology, but are different between synovial fluid, cartilage tissue and cultured chondrocytes. Arthritis Res Ther. 2014 Sep. 26; 16(5):441.

The invention claimed is:

1. A unit dosage form in the form of an orally administered tablet or capsule comprising:
   a) one or a combination of flavonoids consisting of baicalin and catechin; and
   b) a curcuminoid selected from curcumin.

2. The unit dosage form of claim 1, wherein said flavonoids and said curcuminoid inhibit lipopolysaccharides-induced inflammatory response.

3. The unit dosage form of claim 1, wherein said flavonoids and said curcuminoid synergistically inhibit lipopolysaccharides-induced inflammatory response.

4. The unit dosage form of claim 1, wherein the flavonoids are in an amount of from about 200 mg to about 600 mg, and the curcuminoid is in an amount of from about 250 mg to about 750 mg.

5. The unit dosage form of claim 1, wherein the flavonoids are in an amount of from about 200 mg to about 600 mg, and the curcuminoid comprises curcumin, and is in an amount of from about 250 mg to about 750 mg.

6. The unit dosage form of claim 1, wherein the flavonoids are in an amount of from about 200 mg to about 600 mg, and the curcuminoid consists essentially of curcumin, and is in an amount of from about 250 mg to about 750 mg.

7. The unit dosage form of claim 1, wherein the flavonoids are in an amount of about 500 mg, and curcuminoid is in an amount of about 500 mg.

8. The unit dosage form of claim 1, wherein the flavonoids and curcumin have a synergistic-inhibitive effect on a lipopolysaccharides-induced inflammatory response in articular chondrocytes.

* * * * *